US009649332B2

(12) United States Patent
Ushida et al.

(10) Patent No.: US 9,649,332 B2
(45) Date of Patent: May 16, 2017

(54) POLY (β-HYDROXY SHORT-MEDIUM CHAIN FATTY ACID)

(75) Inventors: Kazunari Ushida, Nishinomiya (JP); Masaki Kuriyama, Otsu (JP)

(73) Assignee: EARTHUS, INC., Kyoto (JP)

( * ) Notice: Subject to any disclaimer, the term of this patent is extended or adjusted under 35 U.S.C. 154(b) by 770 days.

(21) Appl. No.: 12/591,209

(22) Filed: Nov. 12, 2009

(65) Prior Publication Data
US 2010/0092422 A1    Apr. 15, 2010

Related U.S. Application Data

(63) Continuation of application No. 10/570,133, filed as application No. PCT/JP2004/012638 on Sep. 1, 2004, now abandoned.

(30) Foreign Application Priority Data

Sep. 1, 2003  (JP) ................................ 2003-308933

(51) Int. Cl.
| | | |
|---|---|---|
| A61K 31/765 | (2006.01) | |
| A61K 31/78 | (2006.01) | |
| A23K 20/158 | (2016.01) | |
| A23L 33/12 | (2016.01) | |
| A61K 9/51 | (2006.01) | |
| A61K 47/34 | (2017.01) | |
| A61K 8/85 | (2006.01) | |
| A61K 9/20 | (2006.01) | |

(52) U.S. Cl.
CPC ............ *A61K 31/78* (2013.01); *A23K 20/158* (2016.05); *A23L 33/12* (2016.08); *A23V 2002/00* (2013.01); *A61K 8/85* (2013.01); *A61K 9/204* (2013.01); *A61K 9/5153* (2013.01); *A61K 47/34* (2013.01)

(58) Field of Classification Search
None
See application file for complete search history.

(56) References Cited

U.S. PATENT DOCUMENTS

| | | | |
|---|---|---|---|
| 4,663,308 A | 5/1987 | Saffran et al. | |
| 4,902,516 A | 2/1990 | Korsatko et al. | |
| 5,206,341 A | 4/1993 | Ibay et al. | |
| 5,229,158 A | 7/1993 | Yalpani et al. | |
| 5,654,009 A | 8/1997 | Hata et al. | |
| 6,207,217 B1 | 3/2001 | Peoples et al. | |
| 6,207,856 B1 | 3/2001 | Veech | |
| 6,251,909 B1 * | 6/2001 | Schnorrenberg et al. | 514/255.03 |
| 6,316,038 B1 | 11/2001 | Veech | |
| 6,323,237 B1 | 11/2001 | Veech | |
| 6,380,244 B2 | 4/2002 | Peoples et al. | |
| 2001/0014696 A1 * | 8/2001 | Veech | 514/449 |
| 2001/0041736 A1 | 11/2001 | Veech | |
| 2002/0013339 A1 | 1/2002 | Martin et al. | |
| 2003/0022937 A1 | 1/2003 | Veech | |
| 2004/0247752 A1 | 12/2004 | Koenig et al. | |

FOREIGN PATENT DOCUMENTS

| | | |
|---|---|---|
| CA | 2069445 | 5/1992 |
| DE | 37 12 095 A1 | 10/1988 |
| EP | 0 285 871 | 6/1992 |
| EP | 0 576 675 A1 | 1/1994 |
| EP | 1 017 379 A1 | 7/2000 |
| EP | 1 045 642 A1 | 10/2000 |
| JP | 63-258810 | 10/1988 |
| JP | 3-83917 | 4/1991 |
| JP | 5-503637 | 6/1993 |
| JP | 06-179618 | 6/1994 |
| JP | H10-324642 | 12/1998 |
| JP | H11-092552 | 4/1999 |
| JP | 2000-143538 | 5/2000 |
| JP | 2001-515510 | 9/2001 |
| JP | 2002-500027 | 1/2002 |
| JP | 2002-521330 | 7/2002 |
| WO | 83/00435 | 2/1983 |
| WO | 92/09211 | 6/1992 |
| WO | 92/09211 A1 | 6/1992 |
| WO | 92/16191 A1 | 10/1992 |
| WO | 98/41201 A1 | 9/1998 |
| WO | 99/34687 | 7/1999 |
| WO | 99/34687 A1 | 7/1999 |
| WO | 00/04895 | 2/2000 |
| WO | 03/028470 | 4/2003 |

OTHER PUBLICATIONS http://bama.ua.edu/~kshaughn/ch338/handouts/exp8-polymerization.pdf.*
Hall et al. Atherosclerosis, 1972, vol. 16, issue 3, 1972, 389-403.*
http://en.wikipedia.org/wiki/Cupriavidus_metallidurans.*
http://en.wikipedia.org/wiki/Ralstonia_eutropha.*
http://en.wikipedia.org/wiki/Treatment_of_Parkinson%27s_disease.*
http://consensus.nih.gov/2010/alzstatement.htm.*
https://en.wikipedia.org/wiki/Inflammatory_bowel_disease printed from web Oct. 22, 2015.*
http://www.niddk.nih.gov/health-information/health-topics/digestive-diseases/crohns-disease/Pages/facts.aspx printed from web Oct. 22, 2015.*
http://www.niddk.nih.gov/health-information/health-topics/digestive-diseases/diarrhea/Pages/facts.aspx#prevent printed from web Oct. 22, 2015.*

(Continued)

*Primary Examiner* — James Rogers
(74) *Attorney, Agent, or Firm* — Wenderoth, Lind & Ponack, L.L.P.

(57) ABSTRACT

The present invention provides a composition comprising a polymer of a β-hydroxy short-medium chain fatty acid, which is used for delivering the β-hydroxy short-medium chain fatty acid or an oligomer thereof to the large intestine. In case the composition is administrated orally, the composition will be delivered to the large intestine, without being degraded in the stomach or short intestine, and degraded by the large intestinal bacterial flora and release the short-medium chain fatty acid or an oligomer thereof. The released short-medium chain fatty acid or an oligomer thereof has useful physiological activities and is effective for treating or preventing inflammatory diseases or cancer in the large intestine.

20 Claims, No Drawings

(56) References Cited

OTHER PUBLICATIONS http://www.niddk.nih.gov/health-information/health-topics/digestive-diseases/constipation/Pages/symptoms-causes.aspx printed from web Oct. 22, 2015.*
https://en.wikipedia.org/wiki/Hyperlipidemia#Management.*
International Search Report issued Nov. 30, 2004 in connection with PCT/JP2004/012638.
Supplementary European Search Report issued Feb. 13, 2009 in connection with EP 04 77 2594.
International Preliminary Report on Patentability issued in PCT/JP2004/012638 corresponding to the present U.S. application.
Cook, S. I. et al., "Review article: short chain fatty acids in health and disease", Allement. Pharmacol. Ther., vol. 12, pp. 499 to 507 (1998).
Niwa, T. et al., "Effect of Dietary Fiber on Morphine-induced Constipation in Rats", Biosci. Biotechnol. Biochem., vol. 66, No. 6, pp. 1233 to 1240 (2002).
Marcil, V. et al., "Butyrate Impairs Lipid Transport by Inhibiting Microsomal Triglyceride Transfer Protein in Caco-2 Cells", J. Nutr., vol. 133, pp. 2180 to 2183 (2003).
Wächtershäuser, A. et al., Eur. J. Nutr., vol. 39, pp. 164 to 171 (2000).
Welters, C. et al., Dis. Colon Rectum, vol. 45, No. 5, pp. 621 to 627 (2002).
Mortensen, F., et al., J. Gastroenterology, vol. 31, pp. 302 to 303 (1996).
Vernia, P. et al., The Lancet, vol. 356, pp. 1232 to 1235 (2000).
Rabbani, G. et al., The Journal of Infectious Diseases, vol. 179, pp. 390 to 397 (1999).
Rahman et al., Gastroenterology, vol. 112, No. 4, A2 (1997).
Ramakrishna, B.S. et al., Gut, vol. 34, pp. 1215 to 1218 (1993).
Rabbani, G. et al., Gastroenterology, vol. 121, pp. 554 to 560 (2001).
Ramakrishna, B.S., The New England Journal of Medicine, vol. 342, No. 5, pp. 308 to 313 (2000).
Kanauchi, O. et al., Biosci. Biotechnol. Biochem., vol. 62, No. 9, pp. 1788 to 1790 (1998).
Chen, H. et al., Nutrition Research, vol. 20, No. 12, pp. 1725 to 1733 (2000).
Chen, H. et al., Journal of the American College of Nutrition, vol. 20, No. 1, pp. 44 to 49 (2001).
Parisi, G. C., Digestive Diseases and Sciences, vol. 47, No. 8, pp. 1697 to 1704 (2002).
Bijkerk, C., Aliment Pharmacol. Ther., vol. 19, pp. 245 to 251 (2004).
Fiordaliso, M. et al., Lipids, vol. 30, No. 2, pp. 163 to 167 (1995).
Delzenne, N. et al., Am. J. Clin. Nutr., vol. 73, pp. 456S to 458S (2001).
Marcil, V. et al. J. Nutr., vol. 133, pp. 2180 to 2183 (2003).
McIntyre, A. et al. Gut, vol. 34, pp. 386 to 391 (1993).
Perrin, P. et al., Gut, vol. 48, pp. 53 to 61 (2001).
D'Argenio, G. et al., Gastroenterology, vol. 110, pp. 1727 to 1734 (1996).
Leschelle, X. et al., Eur. J. Biochem., vol. 267, pp. 6435 to 6442 (2000).
Augenlicht, L. et al., Cancer Research, vol. 59, pp. 6005 to 6009 (1999).
Heerdt, B. et al., Cancer Research, vol. 54, pp. 3288 to 3294 (1994).
Heerdt, B. et al., The Journal of Biological Chemistry, vol. 266, No. 28, pp. 19120 to 19126 (1991).
Pouillart, P., Life Sciences, vol. 63, No. 20, pp. 1739 to 1760 (1998).
Anderson, A., Microbiological Reviews, vol. 54, No. 4, pp. 450 to 472.
Lee, S., Biotechnology and Bioengineering, vol. 49, pp. 1 to 14 (1996).
Brune, V. et al., Z. Tierphysiol., Tierenährg. u. Futtermittelkde., vol. 38, pp. 81 to 93 (1977).
Forni, D. et al., Ann. Zootech., vol. 48, pp. 163 to 171 (1999).
Forni, D. et al., J. Anim. Physiol. A. Anim. Nutr., vol. 81, pp. 31 to 40 (1999).
Forni, D. et al., J. Anim. Physiol. A. Anim. Nutr. 81, pp. 41 to 50 (1999).
Embleton, J. et al., J. Microencapsulation, vol. 9, No. 1, pp. 73 to 87 (1992).
Kusaka, S. et al., Appl. Microbiol. Biotechnol., vol. 47, pp. 140 to 143 (1997).
McBee, R., The Journal of Experimental Zoology Supplement, vol. 3, pp. 55 to 60 (1989).
Stevens, C. et al., Physiological Reviews, vol. 78, No. 2, pp. 393 to 427 (1998).
Marounek, M. et al., Physiol. Res., vol. 47, pp. 259 to 263 (1998).
Jamroz, D. et al., Comparative Biochemistry and Physiology Part A, vol. 131, pp. 657 to 668 (2002).
Kihara, M. et al. Comparative Biochemistry and Physiology Part A, vol. 132, pp. 333 to 340 (2002).
Mountfort, D. et al., Applied and Environmental Microbiology, vol. 68, No. 3, pp. 1374 to 1380 (2002).
Hara, H., Bioscience Microflora, vol. 21, No. 1, pp. 35 to 42 (2002).
Andoh, A. et al., Current Pharmaceutical Design, vol. 9, pp. 347 to 358 (2003).
Harig, J. et al., The New England Journal of Medicine, vol. 320, No. 1, pp. 23 to 28 (1989).
Head, K. et al., Alternative Medicine Review, vol. 8, No. 3, pp. 247 to 283 (2003).
Goh, J. et al., Aliment. Pharmacol. Ther., vol. 17, pp. 307 to 320 (2003).
Hong, J. et al., Aliment. Pharmacol. Ther., vol. 15, pp. 1253 to 1262 (2001).
Jacobasch, G. et al., Int. J. Colorectal Dis., vol. 14, pp. 201 to 211 (1999).
Andoh, A. et al., JPEN, Journal of Parenteral and Enteral Nutrition, vol. 23, No. 5, pp. S70 to S73 (1999).
Kanauchi, O. et al., Journal of Gastroenterology and Hepatology, vol. 14, pp. 880 to 888 (1999).
Slater, S.C. et al., *Journal of Bacteriology*, vol. 170, No. 10, pp. 4431 to 4436 (1988).
Schubert, P. et al., *Journal of Bacteriology*, vol. 170, No. 12, pp. 5837 to 5847 (1988).
Poirier, Y. et al., *Science*, vol. 256, pp. 520 to 523 (1992).
Younes, H. et al., *The Journal of Nutrition*, vol. 125, No. 4, pp. 1010 to 1016 (1995).
Okayasu, I. et al., *Gastroenterology*, vol. 98, pp. 694 to 702 (1990).
Tanaka, Y. et al., *Eur. J. Biochem.*, vol. 118, pp. 177 to 182 (1981).
Mochizuki, M. et al., *Polymers for Advanced Technologies*, vol. 8, pp. 203 to 209 (1996).
Written Opinion of the International Searching Authority in connection with PCT/JP2004/012638.
Richard L. Veech, "The therapeutic implications of ketone bodies: the effects of ketone bodies in pathological conditions: ketosis, ketogenic diet, redox states, insulin resistance, and mitochondrial metabolism", Prostaglandins, Leukotrienes and Essential Fatty Acids, vol. 70, pp. 309-319, (2004).

* cited by examiner

POLY (β-HYDROXY SHORT-MEDIUM CHAIN FATTY ACID)

TECHNICAL FIELD

This application is a Continuation of U.S. application Ser. No. 10/570,133, filed May 3, 2006, now abandoned which is a national stage application of International application No. PCT/JP2004/012638, filed Sep. 1, 2004.

The present invention relates to a method for delivering a β-hydroxy short-medium chain fatty acid monomer or an oligomer thereof to the large intestine by means of oral administration or a procedure parallel to oral administration. The present invention further relates to a composition which is used for delivering a β-hydroxy short-medium chain fatty acid monomer or an oligomer thereof to the large intestine of a subject by means of oral administration or a procedure parallel to oral administration.

Further, the invention relates to a novel animal feeding stuff.

Further more, the invention relates to a pharmaceutical composition and a functional food product useful for keeping or improving physiologic function, for treating or preventing inflammatory bowel disease and for treating or preventing large intestine cancer.

Still further, the invention relates to a coating composition useful for delivering an active ingredient to the large intestine of a subject and releasing the ingredient there.

BACKGROUND ART

The biological effects of short-medium chain fatty acids have been studied recently. It has been revealed that a short chain fatty acid exhibits the physiological actions shown below and a medium chain fatty acid exhibits the 6th action among the list.

1. Promotes growth of intestinal epithelial cells.
2. Activates intestinal movement and ion transportation, i.e. absorption of water and ions.
3. Increases blood flow in the large intestinal mucosa.
4. Increase mucus secretion in the large intestine.
5. Adjusts endocrine secretion, including promotes insulin secretion and prevents catabolic hormone secretion.
6. Promotes pancreatic exocrine function or digestive fluid secretion.
7. Affects on the bacterial flora in the large intestine, including stimulates growth of lactic acid fermentation bacteria and suppress growth of *escherichia colis*.
8. Promotes cell differentiation and apoptosis.

When the short chain fatty acids are orally administered, almost all of the administered acids are absorbed from stomach and small intestine and the acids hardly get to the large intestine. Accordingly, in the conventional studies, oral administration of various resistant starches or water soluble dietary fibers; and enema administration of short chain fatty acids have been employed for delivering the short chain fatty acids to the large intestine. The orally administered resistant starches or water soluble dietary fibers pass through the gastrointestinal tract without being digested, reach to the large intestine, and in the large intestine, part of them are easily digested into short chain fatty acids by the fermentation action of bacterial flora in the large intestine.

In these days, effects of short chain fatty acids, including anti-inflammatory effect, anti-proliferative effect against tumor cells, differentiation enhancing effect and apoptosis inducing effect have been revealed and the short chain fatty acids have been tried or proposed to be applied for treating or preventing a various diseases. For example, non-patent references 1-3 disclose effects of short chain fatty acids on inflammatory bowel disease, diarrhea, colon cancer and the like.

It has been reported that due to its anti-inflammatory effect, a short chain fatty acid is useful for treating inflammatory bowel disease including ulcerative colitis, Crohn's disease, pouchitis, ischemic colitis, diversion colitis, and radiation proctitis. In addition, it has been reported that the short chain fatty acid is effective for treating large bowel cancer because of its apoptosis inducing effect on tumor cells (see non-patent references 4-7).

Among the inflammatory bowel diseases, ulcerative colitis and Crohn's disease, which are associated with formation of erosions or ulcers of unknown etiology, are hard to cure and include repeated active and remission stages. Drug therapy has been tried to inhibit the inflammatory during the active stage and lead the patient to the remission stage, and to prolong the remission stage period. In many studies, administering the short chain fatty acids to the large intestine by means of enema or oral administration of water soluble dietary fibers has been reported effective for preventing or treating said disease (non patent references 8-11).

In addition, effect of the short chain fatty induced by oral administration of water soluble dietary fiber or by the short chain fatty acids enema or intestinal infusion for treating the other inflammatory disease with similar conditions such as diversion colitis, pouchitis, ischemic colitis, radiation proctitis and colitis caused by bacterial infection such as *Shigella* have been reported (non patent references 12-15).

It has been reported that upon treating those diseases with a short chain fatty acid, diarrhea associated with said disease is also relieved. This effect might be due to the water absorption improving effect of the short chain fatty acids. With respect to the effect on diarrhea, it was also reported that oral administration of resistant starch or water soluble dietary fiber, and intestinal infusion of a short chain fatty acid were effective on acute diarrhea including choleraic and non-cholearaic diarrhea, and persistent diarrhea including non-pathogenic diarrhea and infectious diarrhea due to rotavirus, cholera bacterium, *salmonella* or toxic pathogenic *Escherichia coli* infection (non patent references 16-19).

On the other hand, it was also reported that resistant starch and water soluble dietary fiber were effective for improving bowel movement and treating constipation due to the effect of a short chain fatty acid to promote movement of the large intestine (non patent references 20-22).

Oral administration of water soluble dietary fiber to patients suffered from diarrhea-predominant, constipation-predominant or mixed type irritable bowel syndrome has been reported to be effective in relief of the condition. It was also reported that non-water soluble dietary fiber, which is hardly digested by the action of intestinal fermentation and provides only small amount of short chain fatty acids, was not effective on IBS (non-patent references 23 and 24).

Administration of resistant starch has been reported to decrease neutral fats, phospholipids, cholesterols and the like in the blood (non patent references 25 and 26). Non-patent reference 27 proposes the mechanism as follows: the resistant starch is fermented and absorbed in the large intestine, the stimulation is transmitted to the short intestine and the release of fatty acid from the short intestine to the circulation system is suppressed.

Some other effects of a short chain fatty acid such as inhibiting tumor cell growth, promoting cell differentiation and inducing apoptosis have also been reported and based on those effects, many people have tried to use some short chain fatty acids for preventing or treating large bowel cancer such as colon cancer and rectal cancer. To date, many studies on the administration of various dietary fibers for reducing the risk of or preventing the onset of large bowel cancer have been reported. Relationship between the amount of generated short chain fatty acids and the cancer inhibitory effect has been reported and the role of the short chain fatty acids on inhibiting cancer is suggested (non-patent references 28 and 29). Effect of short chain fatty acids enema for preventing onset of cancer has also been reported (non-patent reference 30).

The short chain fatty acid affects differently on different stages of developing tumor from normal epithelial cells thorough adenoma cells. That is, it promotes growth of normal cells and induces apoptosis of adenoma cells. In addition, on the tumor cells, it has been reported to suppress growth, induce apoptosis and promote histone hyperacetylation. The mechanism of the same has been elucidated.

It has been suggested that the short chain fatty acids directly, or some metabolites thereof generated in the pathway through the acetyl CoA synthesis play a role in the suppression of tumor cell growth (non patent reference 31). In addition, apoptosis inducing activity of the short chain fatty acid has been suggested to be associated with β-oxidization of the same in mitochondria (non-patent references 32-34).

It has been known that the short chain fatty acid is converted to the β-hydroxy fatty acid by means of cell mitochondrial β-oxidization. In has also been known that patients with ulcerative colitis in active phase exhibited impaired fatty acid metabolism and that the content of hydrogen sulfide, which suppress β-oxidization of short chain fatty acid, in the patient's stool was high. In addition, the effect of the short chain fatty acid on rat ulcerative colitis was inhibited by simultaneous administration of a β-oxidation inhibitor. (non patent reference 10).

In view of the apoptosis and cell differentiation inducing effect of the short chain fatty acid, 5-fluorourasil, which is metabolized into butyric acid, and ester derivatives, such as glycerides or sugar ester, of short chain fatty acids have been proposed for treating breast cancer, prostate cancer or leukemia. Those studies were aimed to increase the blood concentration of the short chain fatty acid (non-patent reference 35).

As is mentioned above, the art employed oral administration of various resistant starches or water soluble dietary fibers or enema administration of short chain fatty acid in order to apply the short chain fatty acids to the large intestine.

However, all of thus administered resistant carbohydrates are not necessarily converted to short chain fatty acids. Some may be converted to carbon dioxide gas, some may be used for bacterial body and some may be converted to the other organic acids such as lactic acid and succinic acid. The short chain fatty acid production efficiency from the resistant carbohydrates are generally low. In addition, the fermentation speed of the resistant carbohydrates is greatly affected by the manner of intake or the existence form of the same in the food. The production ratio between the short chain fatty acids and the other organic acids could vary greatly, for example, if the fermentation speed increases, the amount of the other organic acids can increase. The other organic acids may affect badly. For example, production or accumulation of a large amount of lactic acid may cause diarrhea.

On the other hand, short chain fatty acid may be applied directly to the large intestine by means of intestinal infusion such as enema. However, such procedure allows only intermittent administration. It is difficult to deliver the acid to entire large intestine by the procedure because there are some parts in the large intestine where the acid cannot reach. In addition, it is also difficult to keep the effective concentration of the injected short chain fatty acid in the large intestine for long time.

To date, no practical procedure for delivering the short-medium chain fatty acid to the large intestine in a controlled manner has been developed.

As a polymer of hydroxy fatty acid, poly(β-hydroxybutyric acid) was firstly found by Lemoigne et al and then, the structure of the polymer and the function as energy storage product and as nutrient or energy source in microorganisms were revealed. After the discovery of copolymer of β-hydroxybutyric acid and β-hydroxyvaleric acid from natural bacteria by Wallen et al, many studies on hydroxy fatty acid polymers have been conducted by the art. (non patent reference 36). Accordingly, it was found that microorganisms produce various hydroxy fatty acid polymers. Hydroxy fatty acid polymers are thermoplastic and proposed to be used for manufacturing biologically degradable plastics.

There are some reports concerning hydroxy fatty acid polymers used as energy storage product for a subject other than microorganisms. Patent reference 1 discloses to use emulsion of polyhydroxyalkanoate having particle size of 0.1-10 μm as fat or cream substitutes based on their texture. This reference is silent about the digestion or metabolite energy of the polymer.

Patent reference 2 discloses animal nutrition composition comprising polyhydroxyalkanoate. This reference discloses that polyhydroxyalkanoate or hydroxy fatty acid polymer increases metabolizable energy content of the food and focused on the energy upon intake the same. However, it is silent about the metabolizing mechanism or metabolizing ratio of the polymer in the animal body. Many microorganisms have enzymes capable of depolymerizing poly(hydroxy fatty acids) (non patent reference 37), but there is no report that an animal produces such a depolymerase.

Patent reference 3 discloses orally administrative polyhydroxycarboxylic acid which is used for lowering pH in the intestinal tract by oral administration of the same. This reference discloses various effect of the polymer and all of them are those predicted from the pH lowering effect. According this reference, α-hydroxycarboxylic acids, especially lactic acid are preferable and polylactic acid was used in the working example. It does not mention β-hydroxy short-medium chain carboxylic acid.

Besides they do not mention degradation of poly (β-hydroxy short-medium chain fatty acids) by bacterial flora in the large intestine or the physiological property of the polymer, there are some reports wherein said polymer were administered to animals (non patent references 38-41). Non-patent reference 38 is a report of a study on microorganism proteins for feeding animals and the reference discloses the effect of poly(β-hydroxybutyric acid) produced by the microorganisms as bi-product on the animals. About 65% of poly(β-hydroxybutyric acid) taken by a pig was recovered from the feces and no residual polymer was found in the organs such as liver, kidney or muscle. Accordingly, about 35% of the polymer was speculated as metabolized in the intestine.

Non-patent reference 39 discloses a study employing a copolymer of β-hydroxybutyric acid and β-hydroxyvaleric acid as metabolizable energy. Said copolymer was hardly metabolized in pigs but the water soluble hydrolysates of the polymer obtained with sodium hydroxide could be metabolized. The reference suggests that the metabolism of the copolymer could vary depending on particle size or crystalline form of the copolymer.

Non-patent references 40 and 41 disclose that copolymers of β-hydroxybutyric acid and β-hydroxyvaleric acid could hardly be metabolized in sheep but copolymers having smaller particle size or hydrolysates of the copolymers could be metabolized. However, they are silent about physiological effects of the copolymer on the sheep.

As above discussed, the art has tried to use poly(β-hydroxy short-medium chain fatty acid) as energy source but the prior arts are silent about the other physiological activities of the polymer.

In order to deliver an active ingredient to the large intestine, compositions having mono- or multiple layer coating or capsulated compositions comprising the active ingredient, which are obtainable by coating the ingredient with film or capsule of a polymer that dissolves under specific pH range, such as methacrylic acid copolymer, or a polymer that is digested by bacterial flora in the large intestine, such as chitosan or aromatic azo moiety comprising polymers have been proposed (patent references 4-7). However, those coatings might be degraded in the small intestine or excreted without being degraded in the large intestine. Further, there are some problems in manufacturing the coatings due to the poor solubility of the used polymers in the less-residual volatile organic solvent.

On the other hand, various references disclosed using poly(hydroxybutyric acid) as matrixes for drug delivery system and formulating the same into implants or microspheres including nanospheres and micro capsules (non-patent reference 42).

Orally or enterally administerable immune modulator, which is to be absorbed by macrophage phagocytosis, comprising microsphere matrix made of poly(hydroxybutyric acid) has been proposed (patent reference 8). The reference discloses microspheres having particle distribution range of 1-15 μm so that macrophages can phagocytize the same. However, the reference does not mention to use the polymer for delivering a drug to the large intestine utilizing the property of the polymer being degraded by bacterial flora in the large intestine.

Non-patent reference 1: Aliment. Pharmacol. Ther., 12, 499-507 (1998)
Non-patent reference 2: Biosci. Microflora, 21, 35-42 (2002)
Non-patent reference 3: Curr. Pharm. Des., 9, 347-358 (2003)
Non-patent reference 4: N. Engl. J. Med., 320, 23-28 (1989)
Non-patent reference 5: Altern. Med. Rev., 8, 247-283 (2003)
Non-patent reference 6: Aliment. Pharmacol. Ther., 17, 307-320 (2003)
Non-patent reference 7: Aliment. Pharmacol. Ther., 15, 1253-1262 (2001)
Non-patent reference 8: Int. J. Colorectal Dis., 14, 201-211 (1999)
Non-patent reference 9: JPEN, J. Parenter. Enteral Nutr., 23, S70-S73 (1999)
Non-patent reference 10: J. Gastroenterol. Hepato., 14, 880-888 (1999)
Non-patent reference 11: Eur. J. Nutr., 39, 164-171 (2000)
Non-patent reference 12: Dis. Colon. Rectum, 45, 621-627 (2002)
Non-patent reference 13: J. Gastroenterol., 31, 302-303 (1996)
Non-patent reference 14: Lancet, 356 (9237), 1232-1235 (2000)
Non-patent reference 15: J. Infect. Dis., 179, 390-397 (1999)
Non-patent reference 16: Gastroenterology, 112, A2 (1997)
Non-patent reference 17: Gut, 34, 1215-1218 (1993)
Non-patent reference 18: Gastroenterology, 121, 554-560 (2001)
Non-patent reference 19: N. Eng. J. Med., 342, 308-313 (2000)
Non-patent reference 20: Biosci. Biotechnol. Biochem., 62, 1788-1790 (1998)
Non-patent reference 21: Nutr. Res., 20, 1725-1733 (2000)
Non-patent reference 22: J. Am. Coll. Nutr., 20, 44-49 (2001)
Non-patent reference 23: Dig. Dis. Sci., 47, 1697-1704 (2002)
Non-patent reference 24: Aliment. Pharmacol. Ther., 19, 245-251 (2004)
Non-patent reference 25: Lipids, 30, 163-167 (1995)
Non-patent reference 26: Am. J. Clin. Nutr., 73, 456S-458S (2001)
Non-patent reference 27: J. Nutr., 133, 2180-2183 (2003)
Non-patent reference 28: Gut, 34, 386-391 (1993)
Non-patent reference 29: Gut, 48, 53-61 (2001)
Non-patent reference 30: Gastroenterology, 110, 1727-1734 (1996)
Non-patent reference 31: Eur. J. Biochem., 267, 6435-6442 (2000)
Non-patent reference 32: Cancer Res., 59, 6005-6009 (1999)
Non-patent reference 33: Cancer Res., 54, 3288-3294 (1994)
Non-patent reference 34: J. Biol. Chem., 266, 19120-19126 (1991)
Non-patent reference 35: Life Sci., 63, 1739-1760 (1998)
Non-patent reference 36: Microbiol. Rev., 54, 450-472 (1990)
Non-patent reference 37: Biotechnol. Bioeng., 49, 1-14 (1996)
Non-patent reference 38: Z. Tierphysiol. Tierenahrg.u. Futtermittelkde., 38, 81-93 (1977)
Non-patent reference 39: Ann. Zootech., 48, 163-171 (1999)
Non-patent reference 40: J. Anim. Phys. Anim. Nutr., 81, 31-40 (1999)
Non-patent reference 41: J. Anim. Phys. Anim. Nutr., 81, 41-50 (1999)
Non-patent reference 42: J. Microencapsulation, 9, 73-87 (1992)
Patent reference 1: WO92/09211
Patent reference 2: WO99/34687
Patent reference 3: Japanese Patent Application Laid Open No. H11-092552
Patent reference 4: WO83/00435
Patent reference 5: Japanese Patent Application Laid Open No. H06-179618
Patent reference 6: Japanese Patent Application Laid Open No. H10-324642
Patent reference 7: U.S. Pat. No. 4,663,308
Patent reference 8: Japanese Patent Application Laid Open No. 2000-143538
The cited references are incorporated herein by reference.

DISCLOSURE OF INVENTION

Problems to be Solved by the Invention

An object of the present invention is to provide a composition used for delivering a physiologically active β-hydroxy short-medium chain fatty acid or a oligomer thereof to the large intestine.

Another object of the present invention is to provide a method for delivering a β-hydroxy short-medium chain fatty acid or an oligomer thereof to the large intestine by means of oral administration or a procedure parallel to oral administration.

Yet another object of the present invention is to provide a novel animal feeding stuff composition.

Still another object of the present invention is to provide a composition useful for treating cancer or inflammatory diseases in the large intestine or for maintaining or improving the intestine function.

Further object of the present invention is to provide a large intestine degradable coating composition, which enables to deliver an active ingredient to the large intestine by means of oral administration or a procedure parallel to oral administration.

Means for Dissolving the Problem

The inventors have discovered that when a poly(β-hydroxy short-medium chain fatty acid) is administered orally to a subject, the polymer reaches the large intestine without being fully digested at stomach or short intestine and degraded by the bacterial flora in the large intestine. Further, inventors have also discovered that a monomer or oligomer of β-hydroxy short-medium chain fatty acid, produced by the bacterial flora degradation of the polymer in the large intestine, exhibits various physiological effects including similar effects as those known in short-medium chain fatty acids and completed the invention.

Accordingly, the present invention provides a composition for delivering a β-hydroxy short-medium chain fatty acid or a oligomer thereof to the large intestine, which comprises a polymer of the β-hydroxy short-medium chain fatty acid.

The invention also provides a method for delivering a β-hydroxy short-medium chain fatty acid or an oligomer thereof to the large intestine of an animal including human, which comprises administering orally a polymer of the β-hydroxy short-medium chain fatty acid to the animal.

Further, the present invention provides use of a polymer of a β-hydroxy short-medium chain fatty acid, for manufacturing a composition for delivering the β-hydroxy short-medium chain fatty acid or a oligomer thereof to the large intestine.

The polymer obtained by polycondensing β-hydroxy short-medium chain fatty acid will not be fully degraded in the stomach or short intestine and the large part of the administered polymer will be delivered to the large intestine. The polymer in the large intestine will be degraded by the bacterial flora there to give water soluble monomer or oligomer of the β-hydroxy short-medium chain fatty acid, the monomer or oligomer will be absorbed from the large intestine and exhibit the physiological activity.

In the present invention, "β-hydroxy short-medium chain fatty acid" represents saturated fatty acid having 3-12 carbon atoms. Preferred examples may include β-hydroxybutyric acid, β-hydroxypropionic acid, β-hydroxyvaleric acid, β-hydroxycaproic acid, β-hydroxycaprylic acid and β-hydroxycapric acid.

According to the present invention, "polymer of a β-hydroxy short-medium chain fatty acid" or "poly(β-hydroxy short-medium chain fatty acid)" may be either a monopolymer of a monomer as above or a copolymer of two or more β-hydroxy short-medium chain fatty acids. Especially, monopolymer of β-hydroxybutyric acid or a copolymer of β-hydroxybutyric acid and one or more of the other β-hydroxy short-medium chain fatty acid monomers may preferably be used. As copolymers, a copolymer of β-hydroxybutyric acid and β-hydroxyvaleric acid is preferably used.

According to the present invention, the poly(β-hydroxy short-medium chain fatty acid) may comprise any monomer unit other than β-hydroxy short-medium chain fatty acid as long as said monomer unit impair the physiological property of monomer or oligomer of the β-hydroxy short-medium chain fatty acid.

According to the present invention, the polymerization degree of the poly(β-hydroxy short-medium chain fatty acid) is not limited as long as the polymer is insoluble to water. When the polymer is water soluble, the orally administered polymer will be absorbed as it is or after hydrolyzed under the acid or alkaline condition in the stomach or small intestine before the polymer reaches the large intestine.

Polymers of a β-hydroxy short-medium chain fatty acid with about 10 or more degree of polymerization are water insoluble. For example, in case of poly(β-hydroxybutyric acids), polymers having 1000 or more weight-average molecular weight are preferably used. The upper limit of the molecular weight of the polymer is not limited and any polymers which can be prepared may be used in the present invention. For example, Appl. Microbiol. Biotechnol., 47, 140-143 (1997) (the cited reference is herein incorporated by reference) discloses that poly(β-hydroxy butyric acid) having weight average molecular weight of 20,000,000 or more was obtained. According to the present invention, the poly(β-hydroxy short-medium chain fatty acids) with polymerization degree of 20-100,000, especially 20-20,000 are preferably used.

In the present application, "oligomer of β-hydroxy short-medium chain fatty acid" represents a water soluble oligomer unless otherwise indicated. Examples of preferred oligomers are those with a polymerization degree of less than 10, more preferably less than 6 and especially less than 3.

The composition of the present invention is useful for treating or preventing various diseases. Those diseases include large bowel cancer such as rectal cancer and colon cancer, inflammatory bowel disease such as ulcerative colitis, Crohn's disease, pouchitis, diversion colitis, radiation proctitis and ischemic colitis.

The composition of the present invention is also useful for treating or preventing diarrhea including diarrhea associated with dysentery or cholera, constipation and irritable bowel disease.

When administered orally or via a route parallel to the oral administration, the composition decreases the neutral fat in the blood and therefore, the composition can be used for preventing or treating hyperlipidemia.

The composition of the present invention has further effect of promoting fat mobilization for utilizing the fat for energy in fasting or starvation. According to this effect, the composition can reduce fat in the body and may be applied for the purpose of losing weight or improving meat quality in livestock animals.

Still further, administration of the composition of the present invention will relieve stress of the subject. In addition, the composition of the present invention is very safe and long term administration of the same will not cause problems.

In another aspect of the present invention, a composition comprising a β-hydroxy short-medium chain fatty acid, an oligomer thereof, or a physiologically acceptable derivatives thereof in a manner that the component is delivered to the large intestine. The phrase "physiologically acceptable derivative" may include acceptable salts and physiologically hydrolyzable derivatives, such as esters and amides, of the β-hydroxy short-medium chain fatty acid or its oligomer and phosphorylated compounds wherein the hydroxy groups are phosphorylated.

Salts may be those with an inorganic ion or an organic base. Examples of inorganic ions may include cations of alkali metals, alkali earth metals and transition metals, for example sodium, potassium, magnesium, calcium, zinc, iron and manganese cations. Examples of organic bases may include trimethyl amine, triethyl amine, ethanol amine, diethanol amine, triethanol amine, and basic amino acids such as arginine, lysine, and ornithine.

Examples of esters may include alkyl esters such as methyl ester, ethyl ester and isopropyl ester, and hydroxyalkyl esters such as hydroxyethyl ester. In addition, esters with saccharides such as mono saccharides and oligo-saccharides and those with polyols such as glycol, glycerol, polyethylene glycol and polypropylene glycol are also used preferably in the invention. Further, phosphate esters with a phosphoric acid such as nucleotides may also be used preferably.

As amides, alkyl amides such as diethyl amide and amides with oligopeptides are preferably used.

As is discussed above, β-hydroxy short-medium chain fatty acids or oligomers thereof are absorbed from stomach or small intestine. However, by formulating the same as large intestine degradable dosage form as of mentioned below or as conventionally known large intestine degradable dosage form, the acid or oligomer thereof can be delivered to the large intestine and exert the physiological effect there. The composition comprising the β-hydroxy short-medium chain fatty acid, an oligomer thereof or a physiologically acceptable derivative thereof in a manner that the component can be delivered to the large intestine will have similar effect as of the above described composition of the present invention comprising a polymer of the β-hydroxy short-medium chain fatty acid.

In further aspect of the present invention, a large intestine degradable coating composition, comprising a poly(β-hydroxy short-medium chain fatty acid) is also provided. The poly(β-hydroxy short-medium chain fatty acids) used for this embodiment may be the same as above described.

According to this application, "large intestine degradable coating composition" represents a coating composition which can provide a dosage form by coating an active ingredient with the composition, wherein the dosage form can deliver the ingredient to the large intestine by means of oral administration or procedure parallel to oral administration of the same without being dissolved in the stomach or short intestine.

According to the present invention, "oral administration or procedure parallel to oral administration" include administration via transnasal tube, gastric administration such as administration directly to stomach or infusion directly to the large intestine in addition to oral administration.

BEST MODE FOR CARRYING OUT THE INVENTION

According to the present invention, the "animal" represent not only mammals including human but also the other vertebrates including fishes and birds. Various bacteria living in the large intestine of vertebrates form the bacterial flora and the bacteria metabolize the food stuff, which are not digested in the stomach or short intestine, by fermentation to give short chain fatty acids and the like. The vertebrates absorb thus generated short chain fatty acids for their energy or nutrition. (J. Exp. Zool. Suppl. 3, 55-60 (1980); Physiol. Rev., 78, 393-427 (1998)). Bacterial flora in the large intestine have been studied in various vertebrates including not only mammals such as human, pig and sheep but also birds such as chickens and ducks and fishes such as carps. The vertebrates, in general, have been revealed to have bacterial flora in the large intestine. Physiol. Res., 47, 259-263 (1998); Comp. Biochem. Physiol. A:Mol. Integr. Physiol., 131, 657-668 (2002); Comp. Biochem. Physiol. A:Mol. Integr. Physiol., 132, 333-340 (2002); and Appl. Environ. Microbiol., 68, 1374-1380 (2002), the cited references are herein incorporated by reference. Accordingly, the composition of the present invention is useful for all vertebrates and especially, for mammal, bird and fish.

According to the present invention, the term "large intestine" represents the digestive tract consisting of cecum, colon and rectum. In some animal species, digestive system is underdifferentiated or underdeveloped and their large and small intestines are indisguishable. In such a case, "large intestine" represents the area where bacterial flora present and fermentation by the bacteria is occurred.

According to the present invention, the poly(β-hydroxy short-medium chain fatty acid) may be prepared by any procedure known to the art. For example, β-hydroxy short-medium chain fatty acid monomer, the starting material, may be polycondensed by means of a conventional polyester synthesizing method.

poly(β-hydroxy short-medium chain fatty acid) produced by microorganism or higher organisms may also be used.

There are many bacteria that produce poly(β-hydroxy short-medium chain fatty acids). For example, see Microbiol. Rev., 54, 450-472 (1990) and Biotechnol. Bioeng., 49, 1-14 (1996), those cited references are incorporated herein by reference. Polymers produced by those bacteria may also preferably be used. Poly(β-hydroxy short-medium chain fatty acids) produced by those bacteria may be isolated from the bacterial cells or may be used together with the cells. In general, bacteria contain a lot of protein and therefore, the composition comprising the polymer together with the cells will be preferable for manufacturing animal feeding stuffs or functional foods.

Among the known microorganisms, *Ralstonia eutropha* and *Alcaligenes latus* have been known to produce a large amount of poly(β-hydroxybutyric acid). Especially, *Ralstonia eutropha* cells having high protein content also contains higher amount of amino acids such as serine and glycine, which are added for the purpose of growth promotion, and therefore had been proposed as protein source. Accordingly, this microorganism will be useful not only for providing poly(β-hydroxybutyric acid) or the like, but also as protein source and are preferable especially for manufacturing animal feeding stuffs or food products.

In addition, gene recombinant techniques enabling a microorganism or a plant, which does not originally produce the desired polymer, to produce the poly(hydroxy fatty acid) have been developed. (J. Bacteriol., 170, 4431-4436, 5837-5847 (1988) and Science, 256, 520-523 (1992), the cited references are herein incorporated by reference). The poly (β-hydroxy short-medium chain fatty acid) used in the present invention may be those obtained from recombinant microorganisms or plants. The polymer may be isolated from the microorganism or plant before adding to the composition of the invention, or the microorganism or plant per se containing the polymer may be added to the composition.

In one embodiment of the present invention, the microorganism comprises at least one trace elements selected from the group consisting of selenium, cobalt, manganese, zinc and copper. In order to incorporate those trace elements in the microorganism, the microorganism may be cultured in a medium comprising the desired elements in the form of a suitable salt. The condition and medium used for the culture are well known to the art and may be determined depending on the microorganism to be used.

According to the present invention, the poly(β-hydroxy short-medium chain fatty acid) is administered orally, transnasaly using transnasal tube, or by means of direct infusion to the large intestine. Oral administration is more easy and practically preferable. In the animal body, the poly(β-hydroxy short-medium chain fatty acid) will be degraded by the bacterial flora in the large intestine. Accordingly, when the composition of the present invention is administered orally, the composition will not be digested or absorbed to provide energy in the small intestine, but the polymer will be delivered to the large intestine, degraded there and utilized.

The water soluble monomers and oligomers produced by the degradation of the poly(β-hydroxy short-medium chain fatty acid) of the present invention are absorbed from the large intestine and exert physiological effects.

By administering the poly(β-hydroxy short-medium chain fatty acid) of the present invention, not only the effects known with short-medium chain fatty acids including inhibition of diarrhea or soft feces, decrease of water content in the feces, promotion of growth and decrease of nitrogen excretion in urine, but also the other novel effects including decrease of the water intake and urine amount, alleviation of fecal odor, increase of the stool frequency, relieve of stress, decrease of gastric and large intestinal retention contents, decrease of small intestine, large intestine and kidney weights, increase of nitrogen accumulation rate and decrease of nitrogen excretion rate were observed.

The inventors have firstly found the facts that poly(β-hydroxy short-medium chain fatty acid) is degraded by bacterial flora in the large intestine and exerts various novel effects other than those conventionally known as the effect of short-medium chain fatty acids.

In another embodiment of the present invention, a composition which can deliver a β-hydroxy short-medium chain fatty acid monomer, a oligomer thereof or a physiologically acceptable derivative thereof. By administering said composition, the β-hydroxy short-medium chain fatty acid monomer or oligomer thereof is delivered to the large intestine and exerts the above described effects.

The composition of the present invention which comprises poly(β-hydroxy short-medium chain fatty acid) and the composition which can deliver a β-hydroxy short-medium chain fatty acid, a oligomer thereof or a physiologically acceptable derivative thereof to the large intestine may be administered to vertebrates in general. The composition of the present invention can be used for various uses associated with activating the large intestine functions.

It has been known that by virtue of short chain fatty acids, which promote the growth and metabolic activity of the bacteria in the large intestine, urea in the blood is transferred to the large intestine, nitrogen uptake into the stool is increased, the fecal nitrogen excreted is increased and urinary nitrogen excretion is decreased. (J. Nutr., 125, 1010-1016 (1995), the cited reference is herein incorporated by reference) The fact has found by the present inventors that in the animals received the composition of the present invention, the ratio of the nitrogen excreted in the feces was decreased and that in urine is increased. Accordingly, the composition of the present invention can reduce or relieve strains on kidney or liver in a patient with renal failure, chronic renal disease or hepatic disease.

In is also revealed that a monomer or oligomer of a β-hydroxy fatty acid monomer, i.e. the degradation products of the composition of the present invention, exhibits tumor cell growth inhibiting activity. This means that by delivering monomer or oligomer of the β-hydroxy short chain fatty acid to the large intestine by administrating the composition of the present invention, the degradation products, β-hydroxy fatty acid or the oligomer thereof exerts the effect similar to that of the conventionally known short chain fatty acid. This fact support the effect of the composition of the present invention for preventing or treating large intestine cancer.

Accordingly, the composition of the present invention comprising a poly(β-hydroxy short-medium chain fatty acid) and the composition comprising a β-hydroxy short-medium chain fatty acid monomer, oligomer thereof or physiologically acceptable derivative thereof in a manner that the component can be delivered to the large intestine may be added to diet or drinking stuff for raised or cultivated mammals, birds or fishes, or may be formulated as an additives for those feeding or drinking stuffs. That is, the composition of the present invention may preferably be used as an animal feeding stuff or an additive for an animal feeding product for maintaining or improving health, promoting growth, reducing odor of faces and urine and facilitating faces and urine disposal of livestock animals, birds, fishes and companion animals.

The composition of the present invention may also be used as functional food product for keeping and controlling the health state and for preventing diseases. In the present application, the term "functional food product" may include supplements, enteral nutritional product, component nutrition product, medical food product, post operative diet and additives thereto. The functional food product may be not only for human but also for animals other than human such as companion animals and livestock animals. In addition, the composition of the present invention may also be used as pharmaceutical composition for preventing or treating constipation and diarrhea, and also for preventing or treating a disease which can be relieved or arrested by means of the various effect of the composition of the present invention.

Accordingly, embodiments wherein the composition of the present invention is provided as a pharmaceutical composition for treating a specific disease, as functional food product for preventing specific diseases or general health maintenance in animals including human and as additive for food or animal feeding product are also in the scope of the present invention.

When the composition of the present invention is provided as pharmaceutical composition or functional food product for an animal including human, it may be formulated as a dosage form suitable for oral administration such as powder, granule, tablet, capsule, sublingual tablet, troche, chewable tablet, dispersion and the like. The dosage form may be manufactured in a conventional manner. The composition of the present invention may be incorporated in food and/or beverage and administered orally.

The composition of the present invention may further comprise a pharmaceutically acceptable additive. Additives are not limited and may be selected from those discloses in general reference books on drug formulation such as excipient, diluent, expander, solvent, lubricant, adjuvant, binder, disintegrating agent, coating agent, capsulating agent, emulsifier, dispersant, suspending agent, thickener, tonicity agent, buffering agent, soothing agent, preservative, antioxidant, corrigent, flavor and colorant based on the requirement.

The composition of the present invention may further comprise the other pharmaceutically active ingredient as long as it will not impair the object of the present invention.

In case the composition of the present invention is manufactured as animal feeding stuff, the formulation of the composition is not limited and may be prepared by adding the poly(β-hydroxy short-medium chain fatty acid) or β-hydroxy short-medium chain fatty acid monomer, oligomer thereof or physiologically acceptable derivative thereof formulated in a manner that the component can be delivered to the large intestine, to a conventional feeding stuff product. The feeding stuff according to the present invention may comprise further physiologically active ingredient unless it will not impair the object of the present invention.

The composition of the present invention may also be formulated as an additive for animal feeding stuff.

In case the polymer used in the present invention is that manufactured by microorganism, the composition of the present invention may comprise whole microorganisms containing the poly(β-hydroxy short-medium chain fatty acid) therein. When the composition comprises the whole microorganism, the microorganism per se will be utilized as protein source. In addition, microorganisms may be prepared with incorporating some essential trace elements in the microorganisms by a conventional procedure simultaneously with producing the poly(β-hydroxy shot-medium chain fatty acid), and thus obtained microorganisms may preferably be added to the composition since not only the protein but also the trace elements from the microorganism can be utilized.

According to the present invention, the amount of the β-hydroxy short-medium chain fatty acid, oligomer thereof or physiologically acceptable derivative thereof in the composition is not limited and may be determined depending on the species, body weight, sex, health condition of the subject to be administered, object of the administration and the like. In general, the amount may be 1 mg-500 mg/kg body weight. The composition of the present invention may be administered all at once or in two or more divided doses. Alternatively, 0.01-5 wt % of the composition may be added to the feeding, drinking or food stuff and administered the stuff to the subject. The amount may be increased or decreased according to the object of the administration.

The present invention further provides a large intestine degradable coating composition, comprising poly(β-hydroxy short-medium chain fatty acid). The coating composition of the invention may be in the form that conventionally used in the pharmaceutical field, such as matrix material for microspheres, coating agent for solid preparation such as tablets, granules, pills and capsules, embedding sheet material for embedding drugs therein or materials for capsules.

The composition degradable in the large intestine may be poly(β-hydroxy short-medium chain fatty acid) which is consisting only of short-medium chain fatty acid or copolymer comprising the other monomer unless said monomer impair the object of the present invention. In addition, additives which are conventionally used in manufacturing medicaments may be added to the composition. Examples of the additives may include aggregation inhibitor, disintegrating agent, lubricant and colorlant. Preferable procedure for manufacturing poly(β-hydroxy short-medium chain fatty acid) is the same as above.

The active ingredient to be delivered to the large intestine is coated with the coating composition of the invention. The coating may be conducted by any of conventionally known procedures, for example, solid or capsule formulation containing the active ingredient may be coated by means pan coating or fluid bed coating, or those active ingredients may be coated by film obtained by a conventional method such as extrusion. In case capsule formulation containing the active ingredient therein is manufactured with the coating composition of the present invention, the capsule may be manufactured by means of a conventional method such as vacuum or pressure forming using a sheet of the composition obtained by extrusion, or by applying and drying the composition to the die. Microspheres may be obtained by means of a conventional method such as drying the polymer in the liquid or spray drying.

The thickness of the coating matrix or the like obtained with the large intestine degradable coating composition can be adjusted by means of any procedure well known to the art based on the object of the administration of the formulation or the kind of the active ingredient.

The active ingredient to be coated by the coating composition of the present invention is not limited and may be any component desired to be delivered to the large intestine. Non limited examples may include protein or peptide compound, which will be inactivated by gastrointestinal enzyme or having an activity similar to insulin which will be absorbed effectively from the large intestine, and various medicaments for the treatment of various diseases in the large intestine.

The present invention will be further explained by the examples below.

EXAMPLE 1

Preparation of Poly(β-Hydroxy Short-Medium Chain Fatty Acid)

REFERENCE EXAMPLE 1

*Ralstonia eutropha* preculture was inoculated in 30 L culture medium shown below and incubated under aeration and agitation at 30° C. During the incubation, the pH was adjusted to 6.8 with aqueous ammonia and the consumed glucose was added accordingly. When the predetermined cell concentration was obtained, aqueous sodium hydrate was added instead of aqueous ammonium to start deposition of the polymer. The culture was incubated for total 3 days with keeping the addition of glucose to provide cells containing poly(β-hydroxybutyric acid). The cells were collected with centrifugation and treated with protease and then with aqueous hydrogen peroxide to isolate the polymer. The polymer was collected, washed with water and dried.

Culture Medium Formulation

| | |
|---|---|
| glucose | 20 g/L |
| ammonium sulfate | 8 g/L |
| magnesium sulfate, heptahydrate | 0.5 g/L |
| potassium sulfate | 1.5 g/L |
| 1N aqueous phosphate | 20 ml |
| minor mineral solution | 50 ml | formulation of the minor mineral solution:

| | |
|---|---|
| calcium chloride, dihydrate | 2.6 g/L |
| ferrous sulfate, heptahydrate | 0.6 g/L |
| copper sulfate, pentahydrate | 20 mg/L |

| | |
|---|---|
| manganese chloride, tetrahydrate | 90 mg/L |
| zinc sulfate, heptahydrate | 100 mg/L |

Thus obtained polymer was analyzed with NMR and confirmed to be poly(β-hydroxybutyric acid). According to the gel permeation chromatography (GPC), the weight average molecular weight of the polymer was 839,000 (calculated as polystyrene) and the yield of the powdery polymer was 58.8 g/L medium.

REFERENCE EXAMPLE 2

The same medium used in reference example 1 2000 L was used and the same microorganism was cultured in the same manner as reference example 1 except for using a mixture of glucose and propionic acid (9:1) in stead of glucose as carbon source for the deposition of the polymer added after the culture reached to the predetermined cell concentration. Thus obtained copolymer was analyzed by NMR and confirmed to comprise 5.4 mol % of β-hydroxyvaleric acid monomer unit. The weight average molecular weight determined with GPC was 737,000 and the yield was 49.8 g/L medium.

REFERENCE EXAMPLE 3

Poly(β-hydroxybutyric acid) was obtained in the same manner as Reference example 1 except for the incubation period was shortened. The polymer was confirmed by NMR and the weight average molecular weight determined with GPC was 869,000. The obtained cells contained 23.6 wt % of the polymer and the dry yield of the cells was 105.4 g/L medium. The nutrition analysis of thus obtained cells are shown in Table 1. As is apparent from table 1, the microorganism containing poly(β-hydroxy short-medium chain fatty acid) is also useful as protein source.

TABLE 1

Nutrition Analysis of the cells comprising poly(β-hydroxybutyric acid).

| Analyzed Item | Content (%) |
|---|---|
| water content | 1.8 |
| crude protein | 64.2 |
| (Conversion Factor: 6.25) | |
| crude lipid | 0.8 |
| crude fiber | 0 |
| crude ash | 3.9 |
| soluble nitrogen content = | 29.3 |
| 100 − the above 5 members | |

EXAMPLE 2

Degradation of the Polymer by the Large Intestinal Bacterial Flora

Cecal fluid of a pig was obtained via cecum cannula, diluted 5 fold with Pipes buffer (pH 6.5) and filtered with gauze. Thus obtained cecal fluid 50 ml was added with the test sample 0.5 g and the mixture was incubated for 24 hours at 37° C. under anaerobic condition (nitrogen 80% and carbon dioxide 20%). After the incubation was completed, the resulting fluid was analyzed by ion chromatography.

As test samples, the powdery poly(β-hydroxy butyric acid) obtained in the reference example 1 and dried cells of *Ralstronia eutropha* containing poly(β-hydroxybutyric acid) obtained in the reference example 3 were used.

According to the ion chromatography analysis, large peaks other than those usually observed in the cecum fluid, which corresponds to the degraded products of poly(β-hydroxybutyric acid) were observed in both samples. The peak was suggested an ester of phosphoric acid and the β-hydroxybutyric acid. The phosphoric acid might be derived from the cecal fluid. The mixture was incubated for further 24 hours and analyzed. Two other large peaks which might be corresponding to the oligomers were observed.

The degradation ratios of the poly(β-hydroxy-butyric acid) samples, which were determined based on the concentrations of the degraded products calculated from the peak areas, were about 30% for the powdery polymer of reference example 1 and about 50% for the dried cells of reference example 3. The difference might be caused from the different surface areas of the poly(β-hydroxybutyric acid) samples based on the different particle sizes.

EXAMPLE 3

Stomach and Small Intestine Bypassing Test

Degradation of the monopolymer of β-hydroxy-butyric acid obtained in Reference Example 1 and the copolymer of β-hydroxybutyric acid and β-hydroxyvaleric acid obtained in Reference Example 2 by commercially available amylase, pepsin, trypsin and lipase were evaluated.

Approximately 100 mg of each polymers was weighted and added to 50 ml of the each aqueous enzyme solution containing 0.1 wt % of the enzyme and adjusted to the pH mimicking the stomach or small intestine environment. The mixture was shaken at 37° C. for the predetermined time, i.e. 6 hours for mimicking the stomach digestion and 10 hours for mimicking the short intestine digestion, and then, filtered and collected.

In each cases, 96% or more of the added polymer was observed after the digestion in the stomach or small intestine mimicking atmosphere. No significant degradation of the polymer was observed. The inventors confirmed by this test that the composition of the present invention are hardly degraded by the acidic or alkaline atmosphere or digestive enzymes in the stomach and small intestine.

Enzyme solutions used in this example were as follows:
Pepsin: Dissolved in gastric Juice mimetic solution (aqueous hydrochloride pH=1.5)
Amylase: Dissolved in gastric juice mimetic solution (aqueous hydrochloride pH=5.5 comprising calcium chloride 0.03 wt %)
Trypsin: Dissolved in small intestinal Juice mimetic solution (aqueous sodium hydrogen carbonate pH=8.0)
Lipase: Dissolved in small intestinal juice mimetic solution (aqueous sodium hydrogen carbonate pH 7.5, comprising calcium chloride 0.03 wt %)

EXAMPLE 4

Two-Week Feeding Test in Rats
Used Rats: 6-weeks old male Wistar rats (n=5)
Control Diet Commercially available pelletized feeding stuff (Labo MR stock, Nosan Corporation, Kanagawa, Japan). The animals could freely eat the diet.
Test Diet: The same pelletized feeding staff as the control diet added with the powdery poly(β-hydroxybutyric acid) obtained in Reference Example 1 in an amount of 5 wt %. The animals could freely eat the diet.
Water: The animals could freely drink water.

Procedure: Each animal was independently kept in a metabolic cage. After the three days acclimatization period, the test and control group animals were received the test diet and control diet respectively ad libitum for two weeks. Every morning at a fixed time, the amount of the remained diet and water were determined and the day's intake was calculated, and then, the diet and water were replaced with the fresh ones. During the last week, the feces was also collected everyday and weighted, then the half of them were dried to determine the water content. The remaining feces was subjected to the ammonia concentration analysis and the like. At the last day, the rats were sacrificed, the organs were weighted according to the standard procedure and the cecal content was analyzed.

The feces was dried for 48 hours at 80° C. and crushed and about 1 g of which was weighted. The dried feces was extracted with 1,2-dichloroethan under heat and reflux, the extract was added with 3 volume of n-hexane to precipitate and collect poly($\beta$-hydroxybutyric acid) and weighted the same. The degradation ratio of the poly($\beta$-hydroxybutyric acid) in the large intestine was calculated from the amount of the polymer remained in the feces.

As a result, the average amount of the polymer in the dried feces was 7.9 wt % and the calculated degradation ratio in the large intestine was 39.3% (SD=6.2%).

From this example, the following effects were significantly ($p<0.05$) observed in the test group (Table 2): Increase of feed conversion ratio (+14%), decrease of water intake (−10%), decrease of water content in the feces (−15%) which cases in decrease of wet weight of the feces, decrease of the total ammonium amount in the feces (−14%), increase of cecum pH, decrease of the stomach content (−61%), decrease of the weight of some organs (small intestine: −19%, kidney: −4%).

In addition, statistical tendency ($p<0.1$) was observed in the following items: increase of the weight gain (+19%), decrease of the cecum content (−24%), decrease of the colon weight (−11%) (table 2).

Those results, i.e. the decreased retention of the ingested materials in the gastrointestinal tract and the decreased weight of some organs suggests that the actual feed efficiency ratio will be greater than the observed value and the muscle and the like in the animal were increased.

Further, a predetermined amount of the cecum content was treated with 70 wt % aqueous perchloric acid and the filtrate was analyzed by ion chlomatography to determine the organic acids in the cecum fluid. There were no substantial difference in terms of the kind and amount of the organic acids between the control and test groups. Even in the test groups, no peak corresponding to the degraded polymer that was observed in the above described in vitro degradation by the large intestinal bacterial flora was observed. Based on the various biological effects observed in the test group, it is suggested that the monomer or oligomer of the $\beta$-hydroxy fatty acid, which is degradation product of the polymer, were absorbed immediately.

Further, the difference confirmed by olfactory and visually observation were follows: less irritating odor in the test group feces, and more freshness color due to the circulating blood of the inner organs such as the large intestine in the test groups.

TABLE 2

RESULTS OF 2-WEEK FEEDING TEST IN RATS

|  | Test Group (SD) | Control Group (SD) |
|---|---|---|
| diet intake (dry weight (g)) | 261.8 (8.4) | 254.3 (23.9) |
| body weight gain (g) | 56.9 (5.2) * | 47.8 (7.6) |
| feed conversion ratio g/g *[1] | 4.63 (0.30) ** | 5.36 (0.41) |
| water intake g/day | 27.2 (1.2) ** | 30.2 (1.6) |
| g/g body weight per day (last 5 days) | 0.152 (0.016) | 0.166 (0.015) |
| water content in the feces (wt %) | 47.7 (5.9) ** | 56.0 (4.6) |
| total ammonia in the feces (mM) | 3.95 (0.79) ** | 4.58 (0.83) |
| pH in the cecum | 6.90 (0.16) ** | 6.47 (0.15) |
| cecum weight (g) | 7.80 (0.75) | 8.63 (1.58) |
| cecum content (g) | 20.70 (6.78) * | 27.29 (4.75) |
| colon weight (g) | 7.17 (0.77) * | 8.05 (0.13) |
| colon content (g) | 8.36 (5.42) | 9.75 (2.07) |
| liver weight (g) | 41.14 (2.21) | 43.72 (5.51) |
| stomach weight (g) | 7.95 (0.82) | 8.19 (0.39) |
| stomach content (g) | 5.55 (2.98) ** | 14.16 (5.84) |
| small intestine weight (g) | 34.75 (5.90) ** | 42.81 (4.27) |
| mesenteric lipids (g) | 9.61 (0.93) | 8.53 (2.25) |
| kidney weight (g) | 8.08 (0.22) ** | 8.41 (0.16) |
| adrenal weight (g) | 0.24 (0.08) | 0.28 (0.08) |
| perirenal fat (g) | 6.94 (1.80) | 6.16 (1.04) |
| spleen weight (g) | 2.38 (0.24) | 2.46 (0.18) |
| heart weight (g) | 3.84 (0.22) | 4.03 (0.27) |
| testes weight (g) | 12.21 (0.38) | 12.22 (0.14) |
| fat around the testis (g) | 8.77 (0.85) | 9.45 (2.62) |

*[1] feed conversion ratio: diet intake (g)/body weight gain(g)
*[2] total ammonium amount in the feces: feces were diluted with pure water and the centrifuged supernatant was analyzed by means of the Indophenol method
* $p < 0.1$
** $p < 0.05$ According to the above, by admixing poly($\beta$-hydroxy short-medium chain fatty acid) in the animal feeding stuff, good effects on the feed efficiency rate, feces odor as well as on the other organs including digestive tract and kidney were observed.

EXAMPLE 5

Feeding Test with Weanling Pigs in Pig Barn

The effect of the present invention for pigs on growth, amount and odor of feces upon feeding in pig barn was examined.
Animals: 24 three-way crossed weanling pigs were used.
Grouping: After the one-week acclimatization period, animals were divided into the test and control groups in consideration of the body weight.
Hosing: Each group was further divided into 3 groups of four pigs (two male and two female pigs each), each group was housed in individual pig barn and fed by ad libitum feeding.
Test Period: Four weeks in the first stage fatten period
Control Diet: Commercially available feeding stuff for weanling pigs (colomeal GS (no antibiotics contained) Nippon Formula Feed Mfg. Co., Ltd., Kanagawa, Japan).
Test Diet: The same feeding stuff as control added with the copolymer of $\beta$-hydroxybutyric acid and $\beta$-hydroxyvaleric acid in an amount of 5 wt %.
Water: animals could freely drink water
Measurement on the followings were made: body weight of individual animal (once per week); diet intake per group (total amount of a week); water intake per group (every day) and feces amount per group (everyday). In addition, appearance of the feces and individual anus were observed visually. The odor of the feces was also measured.

As odor measurement, ammonium, volatile fatty acid, hydrogen sulfide and total mercaptan contained in the feces were measured once a week. The measurement was carried out as follows: one day's feces of each group was collected, put in a plastic bucket and stood for one day without covering the top. After that, 1 kg of the feces was spread on a tray, put the tray in 100 L plastic bag with non-smelled air and kept for 1 hour. Then, the concentration of the respective element in the head space of the bag was measured with a gas detecting tube.

Result of the Feeding Test in Pig Barn

Body weight gain and feed conversion ratio:

The body weight of the animals was increased from around 10 kg at the start to around 25 kg. The test was conducted with weanling pigs during the rapid growth period and there was no significant difference in the test and control groups. However, the feed conversion ratio in the test group was better than the control group in several percent (table 3). As was observed in Example 4, the retention of the ingested materials in the gastrointestinal tract could be decreased also in the test group pigs. This suggests that the substantial body weight including muscle amount and the like might be increased in the test group and caused in the substantial difference in the feed conversion ratio. The result obtained in Example 6 shown below that the higher nitrogen accumulation ratio in the test group is in line with the above suggestion.

TABLE 3

Feeding of Weanling Pigs in Pig Barn (1 month)

| | test group (SD) | control group (SD) |
|---|---|---|
| body weight gain (kg) | 15.1 (1.3) | 15.0 (0.8) |
| diet intake per group (kg) | 135.8 (16.5) | 139.1 (3.2) |
| feed conversion ratio (kg/kg) | 2.25 (0.08) | 2.32 (0.17) |
| water intake (kg) | 454 (118) | 423 (45) |
| feces per group (kg) | 50.0 (9.1) | 49.6 (4.4) |

\* $p < 0.1$
\*\* $p < 0.05$

Effects on Preventing Soft Feces and Diarrhea:

Throughout the feeding period, only two out of 12 animals in the control group excreted normal feces whereas 8 out of 12 animals in the test group excreted normal feces, i.e. the significant effect of inhibiting soft feces and diarrhea was confirmed ($p<0.05$).

Odor of the Excretory Substance:

The odor of the control group was more irritate than that of the test group. Each odorous component are shown in Table 4 below. The declining trend and significant decline of the odor from the excretory substance were confirmed. That is, in the test group, the volatile fatty acid was decreased by about 25% and both hydrogen sulfide and total mercaptan were decreased by more than 40% from those of the control group (Table 4).

TABLE 4

Volatile Odorous Components from the Pig Excretory Substance (4 weeks)

| odorous component (ppm) | test group (SD) | control group (SD) |
|---|---|---|
| Volatile ammonia | 0.8 (0.8) | 0.6 (0.3) |
| Volatile fatty acid: | | |
| 1-4 wk. | 6.9 (3.2) \* | 9.6 (4.1) |
| 3-4 wk. | 4.8 (0.9) \*\* | 6.4 (1.4) |
| hydrogen sulfide | 1.1 (0.9) \* | 1.9 (1.2) |
| total mercaptan | 0.9 (0.6) \* | 1.7 (1.4) |

\* $p < 0.1$
\*\* $p < 0.05$

EXAMPLE 6

Feeding of Pigs in the Metabolite Cage

After Example 5 was completed, each four male pigs were selected for the test and control groups so that pigs of the two groups have approximately the same body weights and housed individually in the metabolic cage. After the 3 days acclimatization period with ad libitum feeding of the same diet, the effect on the feces and urine amount and nitrogen metabolism were examined.

Diet: The same as used in Example 2

Test Period: 5 days

Measurement on the followings were made: body weight of individual animal (before and after the test); diet intake, water intake, feces amount (feces of individual animal was collected every hour. The collected feces were kept in the refrigerator and then one day amount was weighted. After that, the half of the feces was dried and the other half was frozen) and urine amount (urine of individual animal was collected every hour. The collected urine was kept in the refrigerator and the one day amount was weighted. It was acidified with sulfuric acid and kept in the refrigerator.) Analysis on the following were made: The amount of the test sample, water content in the feces and fecal nitrogen excretion (determined by the Kjeldahl method), and urinal nitrogen excretion (determined by the Kjeldahl method).

Result of Feeding in the Metabolite Cage

The amount of the copolymer in the collected feces was determined in the same manner as Example 1. The average amount of the copolymer in the dried feces was 26.3 wt % and the calculated degradation ratio of the copolymer in the large intestine was 52.2% (SD=3.4%).

Observed Effects on the Body: Table 5

In the control group, the diet intake was significantly decreased. In the last stage of pig barn feeding just before this test, the diet intake per day was about 1.4 kg, whereas the diet intake of the control group was decreased by more than 20% in about two days (average, 1.75 days) during the metabolic cage feeding period. In the test group, no decrease in diet intake was observed. The decrease in diet intake observed in the control group is suggested being caused by the stress due to the small space of the metabolic cage. In contrast, the diet intake of the test group was not decreased and the effect of the composition of the present invention as a stress reliever was confirmed.

The average stool frequency observed in the test group of 32.5 was significantly larger (+30%) than that of the control group of 25. This supports the effect of the invention to activate the intestinal movement and provide better excretion.

The urination frequency in both groups was about 40 and there were no significant difference between the groups. The average amount of the urine in the test group of 3,946 g was non-significantly lower (−11%) than that in the control group of 4,452 g. Further, the average water content in the feces of the test group of 62.6% was significantly lower (−10%) than that in the control group of 69.4%.

As is discussed above, the new findings concerning the effects of the present invention including the increase in stool frequency and decrease in the amount of urine were obtained.

TABLE 5

Result of Feeding Pigs in the Metabolite Cage (Five Days)

| | test group (SD) | control group (SD) |
|---|---|---|
| diet intake (kg) | 7.14 (0.44) ** | 6.41 (0.34) |
| body weight gain (kg) | 3.0 (1.0) | 2.9 (0.8) |
| water intake (kg) | 16.1 (3.0) | 16.2 (1.0) |
| feed conversion ratio kg/kg | 2.51 (0.60) | 2.24 (0.65) |
| stool frequency | 32.5 (3.4) ** | 25.0 (4.0) |
| fecal amount g | 1,751 (207) | 1,367 (362) |
| urination frequency | 40.3 (5.1) | 41.5 (9.4) |
| urine amount (g) | 3,946 (132) * | 4,452 (499) |
| water content in the feces (wt %) | 62.6 (2.0) ** | 69.4 (1.1) |

\* $p < 0.1$
\*\* $p < 0.05$

Effects on the Nitrogen Balance

The nitrogen balance was calculated based on the nitrogen amount in the feces and urine determined by the Kjeldahl method, dried ratio of the diet (89.5%), CP value of the diet (26.0%) and the nitrogen amount conversion factor (6.25). Results are summarized in Table 6.

There were no significant difference in the nitrogen intake and nitrogen excretion in the feces and urine. However, there was an increasing trend in the test group with respect to the amount of the nitrogen accumulation in the body. It was 172.0 g in the control group whereas 189.6 in the test group. The body accumulation ratio in the test group was suggested larger than the control group. In order to confirm the suggestion, the results are expressed in percentage in Table 7. According to table 7, some trends were observed in the test group, namely: the nitrogen accumulation in the body was increased and the nitrogen excretion was decreased, and the ratio of the nitrogen excreted in the urine to that in the feces was reduced (i.e. the ratio excreted in the feces was increased). That is, the composition of the present invention is effective for improving feed conversion ratio and increasing muscle amount as well as decreasing urine disposal cost. It is more difficult to treat nitrogen contents in the urine than those in the feces.

TABLE 6

Nitrogen Balance Test in Pigs

| | test group (SD) | control group (SD) |
|---|---|---|
| nitrogen intake (g) | 252.7 (15.6) | 238.5 (12.4) |
| total nitrogen excretion (g) | 63.1 (4.2) | 66.5 (4.7) |
| nitrogen accumulation (g) | 189.6 (13.6) * | 172.0 (7.1) |
| fecal nitrogen (g) | 19.5 (0.8) | 19.4 (1.1) |
| urinary nitrogen (g) | 43.7 (4.0) | 47.1 (3.5) |

\* $p < 0.1$
\*\* $p < 0.05$

TABLE 7

Calculated Nitrogen Balance Test Results

| | | test group (SD) | control group (SD) |
|---|---|---|---|
| nitrogen accumulation rate % | | 75.0(1.4) * | 72.1(2.3) |
| total nitrogen excretion rate (%) | | 25.0(1.4) * | 27.9(2.3) |
| fecal nitrogen excretion rate (%) | | 7.7(0.4) | 8.1(0.6) |
| urinary nitrogen excretion rate (%) | | 17.3(1.4) * | 19.8(1.6) |
| excretion ratio in feces or in urine (%) | in feces | 30.9(1.7) * | 29.1(0.3) |
| | in urine | 69.1(1.7) * | 70.9(0.3) |

\* <0.1,
\*\* <0.05

EXAMPLE 7

Inflammatory Preventing Effect
Used Rats: 8-weeks old male Wistar rats
Diet: See Table 1 The animals could freely eat the diet.
Water: The animals could freely drink water.

TABLE 8

Formula of the diet (g/kg)

| ingredients | control group | test group |
|---|---|---|
| casein | 200 | 200 |
| α-cornstarch | 647 | 647 |
| soy oil | 50 | 50 |
| mineral mix | 40 | 40 |
| vitamin mix | 10 | 10 |
| DL-methionine | 3 | 3 |
| cellulose | 50 | — |
| poly(β-hydroxybutyric acid) | — | 50 |

The poly(β-hydroxybutyric acid) used herein was that obtained in Reference Example 1.

Feeding: The animals were fed with commercially available pelletized feeding stuff, Labo MR stock, Nosan Corporation Kanagawa, Japan for 3 days of acclimatization. Then, the animals were divided into two groups and fed with the respective diet for 2 weeks. After that, the respective diets were exchanged with colitis-inducing diet according to Gastroenterology, 98, 694-702 (1990) (the cited reference is herein incorporated by reference); i.e. the amount of cornstarch in each diet was reduced to 617 g/kg and dextran sodium sulfate (DSS) in an amount of 3 wt % was added. The animals were fed further.

The day when bloody stool was observed for the first time was recorded and on the following day, the animal was sacrificed and subjected to autopsy. Individuals without bloody stool were kept feeding with the DSS containing diet for 14 days and subjected to autopsy on the 15th day. Upon the autopsy, the each organ was weighted and visually observed. In addition, tissue slice of the large intestine was prepared and the tissue was observed with optical microscope. The histopathological evaluation of the inflammatory was made according to the 4-scale evaluation criteria:
0: normal, 1: dotted inflammation, 2: diffused inflammation, 3: inflammation all over the tissue.
The degree of the bleeding was evaluated according to the 3-scale evaluation criteria:
0: normal, 1: local and 2: all over the tissue.

There were no significant difference between the test and control groups in terms of the diet intake and weight gain. During the DSS administration and control group surviving period, there were no significant difference between the groups in terms of the diet intake and weight gain. From 5 to 7 days after the diets were exchanged with those containing DSS, bloody stool was observed in all 8 animals in the control group. In the test group, bloody stool was observed in one animal on day 7 and even at the 14th day, no bloody stool was observed in 4 out of 7 animals in the test group. That is, with respect to occurrence of bloody stool, significant difference was observed from the 7th day. With respect to the inflammatory, significant erosion and bleeding inhibitions were observed in the lower large intestine (rectum), the area where DSS-induced inflammation occurs most intensively, of the test group and the inflammatory preventive effect of the present invention was confirmed.

TABLE 9

Inflammatory Preventive Test Result

|  | test group (SD) n = 7 | control group (SD) n = 8 |
|---|---|---|
| weight of the colon (g) | 1.90 (0.21) ** | 2.25 (0.23) |
| the first day of bloody stool, from the start of DSS administration (day) | 11.3 (2.6) ** | 6.3 (0.7) |
| rectum erosion score | 1.0 (0.0) ** | 2.6 (0.7) |
| rectum bleeding score | 0.1 (0.4) ** | 0.9 (0.4) |

* $p < 0.1$
** $p < 0.05$

EXAMPLE 8

Inflammation Treating Test

Used Rats: 8-weeks old male Wistar rats (total 16 animals, n=8 for each group)

Diet: The animals could eat freely the diet.

Water: The animals could freely drink water.

Feeding: The animals were fed with commercially available pelletized feeding stuff, MF, Oriental East Co., Ltd. Tokyo, Japan for 3 days of acclimatization. Then, the animals were fed with the control diet shown in Table 8 for 4 days for taming them to the powdery diet. And then, the diet was exchanged with the colitis inducing diet wherein the amount of cornstarch was reduced to 617 g/kg and dextran sodium sulfate (DSS) in an amount of 3 wt % was added and the animals were fed further.

At the date when bloody stools were observed two successive days, the animals were divided into control and test groups and fed with the respective diet shown in table 8 for 7 days. After that, all animals were sacrificed and subjected to autopsy. Each organ was weighted and visually observed. In addition, tissue slice of the large intestine was prepared and the tissue was observed with optical microscope. The histopathological evaluation of the inflammatory was made in the same manner as Example 7.

There were no significant difference between the test and control groups in terms of the erosion in the portion other than cecum. In the cecum, erosion was observed in 5 out of 8 control animals whereas only one out of 8 test animals. This result suggests the effect for treating inflammatory of the composition of the present invention ($p<0.1$).

EXAMPLE 9

High Cholesterol Diet

Used Rats: 6-weeks old male Sprague-Dawley rats (n=8 for each group)

Diet: The animals could freely eat the diet. The control group was fed with the basic diet (table 10) and the test group was fed with the basic diet added with 5 wt % of the poly(β-hydroxybutyric acid).

Water: The animals could freely drink water.

TABLE 10 basic diet formulation(g/kg)

| ingredients | amount |
|---|---|
| casein | 200 |
| α-cornstarch | 543.5 |
| soy oil | 40 |
| lard | 100 |
| mineral mix | 40 |
| vitamin mix | 10 |
| DL-methionine | 3 |
| choline chloride | 1 |
| cholesterol | 10 |
| sodium cholate | 2.5 |

Feeding: The animals were fed with commercially available pelletized feeding stuff, Labo MR stock, Nosan Corporation Kanagawa, Japan for 3 days of acclimatization. After that, the animals were fed with the basic diet shown in Table 10 twice a day, between 9 and 10 o'clock, and between 21 and 22 o'clock, for 4 days of acclimatization. After the acclimation period was terminated, the animals were divided into two groups. The test and control groups were fed with the respective diet twice a day for 2 weeks. The control group was fed with the basic diet in an amount 95 wt % of the average intake amount of the test group so that there is no difference between the control and test groups in terms of the intake of the ingredient in the basic diet (pair feeding design). After the last feeding (between 21 and 22 o'clock on the last day), the animals were fasted and from half past 13 o'clock on the following day, blood was collected from the abdominal aorta and total cholesterol, neutral fat and free fatty acid in the blood were examined. During the test period, there was no significant difference between the groups in terms of the diet intake and body weight gain. Results are shown in Table 11.

TABLE 11

Result of high fat diet feeding(1)

|  | Test Group (SD) | Control Group (SD) |
|---|---|---|
| neutral fat (mg/dL) | 48 (20) * | 79 (37) |
| free fatty acid (mg/dL) | 1057 (186) * | 881 (148) |
| total cholesterol (mg/dL) | 283 (89) | 266 (114) |

* $p: <0.1$
** $p < 0.05$

In the test group, decrease of serum neutral fat (about 39%) and increase of free fatty acid (about 20%) were observed. The fat mobilization, degradation of body fat, was promoted under the fasting condition. There were no significant difference between the groups in terms of the diet intake and body weight gain.

In addition, animals (n=15) were fed in the same manner as above but fed in the morning (between 9 and 10) on day 14 and from half past 13 o'clock on the same day, blood was collected from the abdominal aorta. Total cholesterol, neutral fat and free fatty acid in the blood were examined. There were no significant difference between the groups in terms of the diet intake and body weight gain. Results are shown in Table 12. There were no significant difference between the groups in terms of the neutral fat and free fatty acid amount.

TABLE 12

| Result of high fat diet feeding(2) | | |
|---|---|---|
| | test group (SD) | control group (SD) |
| neutral fat (mg/dL) | 156 (39) | 207 (57) |
| free fatty acid (mg/dL) | 948 (244) | 982 (197) |

EXAMPLE 10

Effect of β-Hydroxybutyric Acid on Large Intestine Cancer

Cell line HT-29 derived from colon tumor was inoculated into McCoy's SA medium supplemented with 10% fetal calf serum comprising penicillin 50 U/ml, streptomycin 50 μg/ml and HEPES 10 mM on 96-well cell culture plate (7,500 cells/well). The cells were pre-incubated in an atmosphere of 95% air and 5% carbon dioxide at 37° C. for 24 hours. Then, various amount of butyric acid, which has been known to have differentiation and apoptosis inducing effects, was added as a positive control. As decomposed components of the present composition, various amount of R(−)-β-hydroxy-butyric acid, S(+)-β-hydroxybutyric acid and dimer of R(−)-β-hydroxybutyric acid were added (all were in the form of sodium salt). The R(−)-β-hydroxybutyric acid dimer was prepared by purification of oligomers of R(−)-β-hydroxy-butyric acid, which was prepared according to Eur. J. Biochem., 118, 177-182 (1981) (the cited reference is herein incorporated by reference), by column chromatography. The plate was incubated further 72 hours. The cell number in the each well was determined by the MTT method based on the difference of the optical density. The results are shown in Table 13.

TABLE 13

| Growth Inhibition against colon tumor cell line | | | | |
|---|---|---|---|---|
| | 0.1 mM | 0.5 mM | 1 mM | 2 mM |
| butyric acid | 0.234 ± 0.012** | 0.243 ± 0.009** | 0.250 ± 0.010** | 0.200 ± 0.009** |
| R-β-hydroxy-butyric acid | 0.271 ± 0.028** | 0.264 ± 0.019** | 0.272 ± 0.015** | 0.284 ± 0.023* |
| S-β-hydroxy-butyric acid | 0.257 ± 0.035** | 0.255 ± 0.013** | 0.281 ± 0.017** | 0.293 ± 0.022* |
| R-dimer | 0.288 ± 0.019* | 0.251 ± 0.029** | 0.248 ± 0.029** | 0.237 ± 0.019** |
| none(cont.) | | 0.337 ± 0.055 | | |

*p < 0.1
**p < 0.05

According to the result shown in Table 13, similarly to the butyric acid added group, the cell number in the group added with β-hydroxybutyric acid or the oligomer thereof was significantly lower than that of the control group. This result shows the cell growth inhibiting effect of β-hydroxybutyric acid and a oligomer thereof.

EXAMPLE 11

Coating Composition

Fluid bed coating machine (Freund Corporation, Tokyo, Japan) was used. Granular food dye Red No. 102 of approximately 0.5 mm diameter was coated using 2w/v % solution of the copolymer obtained in Reference Example 2 in methylene chloride by spraying the solution to the granule for 1 hour. The obtained coated food dye had 40 wt % of coating ratio and about 30 μm of calculated coating thickness. The coating ratio represents the ratio of the weight of coating composition to that of the food dye.

The coated food dye was put in the gastric juice and small intestinal juice mimetic solutions used in Example 3 at 37° C. and stirred gently. The dye leakage from the coated food dye was observed visually over time.

In addition, the cecal fluid of pig, which was diluted 5 fold with Pipes buffer pH 6.5 used in Example 2 was used. The coated food dye was added to the cecal fluid at 37° C. and stirred gently under anaerobic condition. The dye leakage from the coated food dye was observed visually over time.

No leakage of the dye was observed during the test period in the gastric juice mimetic solution (6 hours) and in the small intestinal Juice mimetic solution (10 hours). Whereas, in the cecal fluid, dye leakage was observed at 4 and half hours. Those results means the coating film of the present invention will not be degraded under the gastric or small intestinal condition and will be degraded by large intestinal bacterial flora.

The invention claimed is:

1. A method for treating a disease condition selected from the group consisting of inflammatory bowel disease, diarrhea, constipation, irritable bowel syndrome and large bowel cancer,
    comprising:
    administering a composition comprising an effective amount of a water-insoluble polymer of a β-hydroxy saturated fatty acid having 3 to 12 carbon atoms that has a degree of polymerization of 10 or more to an animal in need thereof,
    wherein the administration is oral, via a transnasal tube, by direct administration into the stomach, or by direct infusion into the large intestine, and
    wherein the composition is in a form selected from the group consisting of a powder, a granule, a tablet, a capsule, a sublingual tablet, a troche, a chewable tablet and a dispersion.

2. The method of claim 1, wherein the water-insoluble polymer is administered orally to the animal.

3. The method of claim 1, wherein the β-hydroxy saturated fatty acid having 3 to 12 carbon atoms is selected from the group consisting of: β-hydroxybutyric acid, β-hydroxypropionic acid, β-hydroxyvaleric acid, β-hydroxycaproic acid, β-hydroxycaprylic acid, β-hydroxycapric acid, and a mixture thereof.

4. The method of claim 1, wherein the water-insoluble polymer is a monopolymer of a β-hydroxy saturated fatty acid having 3 to 12 carbon atoms.

5. The method of claim 1, wherein the water-insoluble polymer is a copolymer of β-hydroxy saturated fatty acids having 3 to 12 carbon atoms.

6. The method of claim 1, wherein the water-insoluble polymer is a monopolymer or copolymer comprising β-hydroxybutyric acid residue.

7. The method of claim 1, wherein the weight average molecular weight of the water-insoluble polymer is in the range of 1,000-20,000,000.

8. The method of claim 1, wherein the water-insoluble polymer is produced by a microorganism.

9. The method of claim 8, wherein the microorganism is administered to the animal.

10. The method of claim 9, wherein the microorganism contains at least one member selected from the group consisting of selenium, cobalt, manganese, zinc and copper.

11. The method of claim 1, wherein the water-insoluble polymer is produced by a plant.

12. The method of claim 11, wherein the plant is administered to the animal.

13. The method of claim 1, wherein an animal feedstuff containing the water-insoluble polymer or an animal feedstuff with an additive containing the water-insoluble polymer is administered to the animal.

14. The method of claim 1, wherein a functional food product containing the water-insoluble polymer is administered to the animal.

15. The method according to claim 1, wherein the disease condition is inflammatory bowel disease.

16. The method according to claim 1, wherein the disease condition is diarrhea.

17. The method according to claim 1, wherein the disease condition is constipation.

18. The method according to claim 1, wherein the disease condition is irritable bowel syndrome.

19. The method according to claim 1, wherein the disease condition is large bowel cancer.

20. The method of claim 1, wherein the animal is a human.

* * * * *